United States Patent [19]

Richter

[11] 4,283,533
[45] Aug. 11, 1981

[54] N-TYPE BETAINES OF 2-HYDROXY-1,1,2,3,3-PENTAHYDROPERFLUOROALKYLAMINES

[75] Inventor: John W. Richter, Kennett Square, Pa.

[73] Assignee: E. I. Du Pont de Nemours and Company, Wilmington, Del.

[21] Appl. No.: 92,767

[22] Filed: Nov. 9, 1979

[51] Int. Cl.$^3$ .................... C07D 265/30; B01F 17/28
[52] U.S. Cl. ............................ 544/171; 260/501.13; 544/399; 546/248; 252/356; 562/568
[58] Field of Search ............... 260/501.13; 562/568; 544/171, 399; 546/248

[56] References Cited

U.S. PATENT DOCUMENTS

| | | | |
|---|---|---|---|
| 3,689,470 | 9/1972 | Shachat et al. | 260/501.13 |
| 3,798,265 | 3/1974 | Bartlett | 562/568 |
| 4,090,969 | 5/1978 | Koch et al. | 260/501.13 |
| 4,165,338 | 8/1979 | Katsushima et al. | 260/567.6 F X |

OTHER PUBLICATIONS

Chambers, "Fluorine in Organic Chem.", John Wiley & Sons, N.Y., 64–67 (1973).

Research Disclosure, Industrial Opportunities Ltd., Hampshire, UK, No. 175, pp. 5–6, Nov. 1978.

*Primary Examiner*—G. T. Breitenstein

[57] ABSTRACT

Amphoteric N-type betaines represented by the formula:

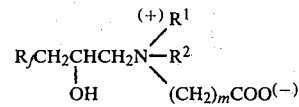

wherein:
$R_f$ is $C_4$–$C_{20}$ perfluoroalkyl;
$R^1$ and $R^2$ are methyl or, together with the N atom to which they are bonded, form a piperidino, morpholino, or
N-alkyl($c_1$–$C_4$)piperazino group; and m is a whole number between 1 and 4 are highly effective in reducing the surface tension of water and of aqueous solutions of inorganic electrolytes, and can be used in environments where non-amphoteric surfactants would fail, e.g. highly acidic oil well applications.

4 Claims, No Drawings

N-TYPE BETAINES OF 2-HYDROXY-1,1,2,3,3-PENTAHYDROPERFLUOROALKYLAMINES

BACKGROUND OF THE INVENTION

1. Field of the Invention

This invention relates to amphoteric N-type betaines of 2-hydroxy-1,1,2,3,3-pentahydroperfluoroalkylamines and their use as surfactants.

2. Description of the Prior Art

Katsushima et al., in U.S. Pat. No. 4,165,338, disclose hydroxy compounds having the formula:

$$Q(N-CH_2CH(OH)CH_2R_f)_m$$

wherein Q is hydrogen; —CH$_2$CH(OH)CH$_2$Rf or a hydrocarbon residue which may contain one or more of

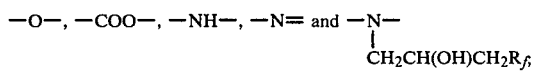

—O—, —COO—, —NH—, —N= and —N—
$\qquad\qquad\qquad\qquad\qquad\qquad\qquad\quad$ |
$\qquad\qquad\qquad\qquad\qquad\qquad\qquad\quad$ CH$_2$CH(OH)CH$_2$R$_f$;

R is hydrogen, a hydrocarbon residue or —CH$_2$CH(OH)CH$_2$R$_f$; m is 1 or 2; R$_f$ is hydroperfluoroalkyl, or ω-chloro-perfluoroalkyl having 4 to 20 carbons. Among the compounds disclosed by Katsushima et al., are ones having the formula:

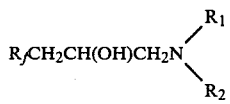

$$R_fCH_2CH(OH)CH_2N\begin{matrix}R_1\\ \\R_2\end{matrix}$$

wherein R$_1$ and R$_2$ are each hydrogen or hydrocarbon group, including CF$_3$(CF$_2$)$_6$CH$_2$CH(OH)CH$_2$N(C$_2$H$_5$)$_2$ and CF$_3$(CF$_2$)$_6$CH$_2$CH(OH)CH$_2$N(CH$_3$)$_2$, among others. Katsushima et al. disclose acid addition salts of their compounds, but no betaine is disclosed.

Cords, in U.K. Patent Specification No. 1,434,119 discloses fluorinated sulfides having the formula $$F(CF_2)_nCH_2CH_2SCH_2CH_2N^+R_1R_2R_3$$

wherein each of R$_1$ and R$_2$ is C$_1$–C$_4$ alkyl; R$_3$ is C$_1$–C$_4$ alkyl or is the covalently bonded counterion —(CH$_2$)$_q$SO$^-$$_3$ or —(CH$_2$)$_m$COO$^-$; m is 1 to 3; n is 4 to 14; and q is 2 to 4.

This invention overcomes a number of disadvantages associated with the compounds of Katsushima et al. and Cords. In the first place, the compounds of Katsushima et al. are not surface active unless reacted with an acid. Moreover, the compounds of Katsushima et al. are never amphoteric, and consequently, they may be used, if at all as surfactants, only under narrowly limited conditions of pH; i.e. less than a pH of about 5. The quaternary ammonium compounds of Cords would be similarly limited. While Cords' betaines would not be limited in that fashion, the process for preparing them (as well as his quaternaries) is a complicated, multi-intermediate procedure which involves certain hazards. Thus, the 2-chloroethyl dialkylamine hydrochloride used to prepare the perfluoroalkyl thioalkyl intermediate is a nitrogen mustard, i.e., an active vesicant. A corrosive system (a thionyl chloride reaction) is involved in preparing the nitrogen mustard intermediate. The 2-perfluoroalkyl ethanethiol is prepared by reacting the corresponding iodide with thiourea, an experimental carcinogen.

DETAILED DESCRIPTION OF THE INVENTION

The amphoteric N-type betaines of this invention are represented by the formula:

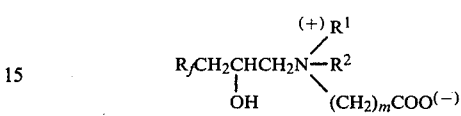

$$R_fCH_2CHCH_2N\begin{matrix}^{(+)}R^1\\ \\ \ \ \ -R^2\\ \\(CH_2)_mCOO^{(-)}\end{matrix}$$
$\qquad\qquad\quad$ |
$\qquad\qquad\quad$ OH wherein R$_f$ is C$_4$–C$_{20}$ perfluoroalkyl;

R$^1$ and R$^2$ are methyl or, together with the N atom to which they are bonded, form a piperidino, morpholino, or N-alkyl(C$_1$–C$_4$)piperazino group; and m is a whole number between 1 and 4.

The betaines of this invention are highly effective in reducing the surface tension of water and of aqueous solutions of inorganic electrolytes. Because they are amphoteric, they can be used in environments where non-amphoteric surfactants would fail, e.g. highly acidic oil well applications.

This invention contemplates single compounds having the foregoing formula as well as mixtures thereof. Usually, the latter are prepared and used because the starting material which provides the perfluoroalkyl portion of the molecule is most commonly available commercially as a mixture. The usual commercial mixture will contain small amounts (less than 5% by weight) on both ends of the foregoing carbon chain length range, with 80 to 90% of the chains containing 6 to 12 carbons, preferably 6 to 10 carbons, with an average in the mixture between 6 and 8 carbons.

The betaines of this invention can be prepared by reacting the corresponding tertiary amine with alkaline metal salts of monochloro or monobromo acetic acid, e.g. sodium chloroacetate, potassium bromoacetate and the like. The reaction of the tertiary amine with the alkaline metal chloro or bromo acetate can be run in any liquid which will serve as a polar solvent for the amine; e.g. glacial acetic acid, methylethyl ketone, isopropanol, water/isopropanol, and the like.

Some of the dialkyl tertiary amines, from which some of the betaines of this invention are derived, are disclosed by Katsushima et al., supra. Those amines, as well as the others which serve as starting materials for the betaines of this invention, can be prepared by the reaction:

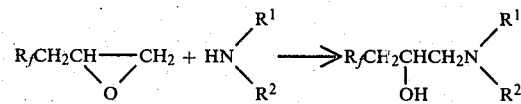

$$R_fCH_2CH\underset{O}{\overset{\diagup}{-\!\!\!-\!\!\!-}}CH_2 + HN\begin{matrix}R^1\\ \\R^2\end{matrix} \longrightarrow R_fCH_2CHCH_2N\begin{matrix}R^1\\ \\R^2\end{matrix}$$
$\qquad\qquad\qquad\qquad\qquad\qquad\qquad\qquad\qquad\qquad$ |
$\qquad\qquad\qquad\qquad\qquad\qquad\qquad\qquad\qquad\qquad$ OH The epoxide starting material for the foregoing reaction can be prepared by reacting an alkaline metal hydroxide with 3-perfluoroalkylpropylene iodohydrin, having the formula:

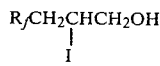

Some of the iodohydrins are known compounds; Katasushima et al. disclose some of them and their preparation. Moreover, they can be prepared, as is more particularly described in the examples hereof by reacting the appropriate perfluoroalkyl iodide with triallyl borate in the presence of a free radical initiator, following which the resulting borate is hydrolyzed to the iodohydrin.

The following examples are given by way of illustration not limitation. Unless specified otherwise, all parts and percentages are by weight and temperatures are in centigrade.

PREPARATION OF TRIALLYL BORATE

A mixture of 445.3 g. (7.2 moles) of boric acid, 2088 g. (36 moles) of allyl alcohol and 697 g. of toluene was refluxed at a pot temperature of 90°–105° and atmospheric pressure, using a column packed with 0.25 inch glass beads to effect separation, and a Dean-Stark separator to remove the by-product water from the solvent. Reflux was continued until no more water was collected in the Dean-Stark separator (27 hours). The product mixture was topped to a pot temperature of 145° to remove toluene and excess alcohol. The residue was distilled in vacuo through a 5-plate Oldershaw to yield 1287.4 g (98.2% of theory) of a colorless liquid product distilling at 62°–63° and 6.0 mm absolute mercury pressure.

PREPARATION OF 3-PERFLUOROALKYLIODOHYDRINS

A mixture of perfluoroalkyl iodides was used which had the characteristics given below. The mixture was analyzed by gas chromatography, using a Perkin-Elmer Model 3920 flame ionization gas chromatograph, a 12′×18″ stainless steel column packed with 20% GE SE-30 silicone on 80/100 Chromosorb W-HP and a program of heating from 50° C. to 260° C. at 16° C./minute. The homolog distribution was expressed as area % and the average molecular weight calculated therefrom to give the following:

| | |
|---|---|
| Unknowns | 1.9% |
| $C_4F_9I$ | 1.6% |
| $C_6F_{13}I$ | 48.2% |
| $C_8F_{17}I$ | 41.0% |
| $C_{10}F_{21}I$ | 6.7% |
| $C_{12}F_{25}I$ | 0.6% |
| $C_{14}F_{29}I$ | <0.1% |

Average molecular weight as $R_fI = 502.8$.

A mixture of 1296 g. (2.58 moles) of the above-described $R_fI$, 156.4 g (0.86 moles) of triallyl borate and 300 g. of methyl ethyl ketone was heated to 65°±2°. "Vazo" 64 azobisisobutyronitrile was added (2.1 g.; 0.013 mole); there was a barely discernible but definite exotherm lasting approximately 15 minutes. The reaction temperature was adjusted to 69°±4°, and the charge was agitated at that temperature for about 18 hours, followed by addition of increments of "Vazo" 64 and triallyl borate at intervals as follows: 2.1 g. of "Vazo" 64; 7 hours later—39.1 g. (0.215 mole) of triallyl borate and 2.1 g. of "Vazo" 64; 17 additional hours—39.1 g. of triallyl borate and 2.1 g. of "Vazo" 64; 28 hours thereafter—2.1 g. "Vazo" 64; and 8 hours later—1.05 g. of "Vazo" 64. After a total of 96 hours, the charge was sampled and the sample hydrolyzed with aqueous acetone and the hydrolyzed sample extracted into "F-113" 1,1,2-trichloro-1,2,2-trifluoroethane. Gas chromatographic analysis of the "F-113" layer showed essentially 98.6% conversion of $R_fI$ to 3-perfluoroalkyl-propylene iodohydrins. The charge was added to 1300 g. of water; the mixture was steam stripped through a 5-plate Oldershaw column to a head temperature of 92° (pot temp. 96°+) to remove unreacted allyl alcohol and the major portion of the MEK. The two phase still residue was separated at ~90°, the lower (product) layer being bottled and the upper (aqueous) layer being discarded, to yield 1431 g. (91%) of a pale yellow oil which solidified on cooling.

| | |
|---|---|
| $C_4F_9CHICH_2OH$ | 1.4% |
| $C_6F_{13}CH_2CHICH_2OH$ | 48.9% |
| $C_8F_{17}CH_2CHICH_2OH$ | 34.4% |
| $C_{10}F_{21}CH_2CHICH_2OH$ | 5.5% |
| MEK and other non-iodohydrins | 9.7% |

Average molecular weight as

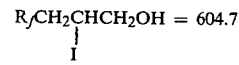

EXAMPLE 1

Preparation of (3-perfluoroalkyl-2-hydroxypropyl)morpholines

A mixture of 362.8 g. (0.6 mole) of 3-perfluoroalkyl-propylene iodohydrins and 441 g. of t-butanol was warmed to 35°–40° to effect solution and then cooled to 23°, and 74 g (0.66 mole) of 50% aqueous potassium hydroxide were added in eight equal increments at 0.5 hour intervals, the temperature being reduced to 5°±5° over the first 1.5 hours and held there. Approximately 20 minutes after the seventh KOH addition, 74.8 g. of morpholine (0.86 mole) were added. The charge was agitated for 18 hours at 5°±5°, after which 8.3 g. of sodium dihydrogen phosphate monohydrate (0.06 mole) was added to neutralize excess potassium hydroxide. Cooling was discontinued, the charge permitted to come to 25°±3° and then it was agitated at that temperature for 20 hours and at 60°±2° for 8 hours. Gas chromatographic assay at that point having showed conversion of iodohydrin to amine adduct to be incomplete, agitation at 80°±2° was continued for 4 more hours, at which point, sampling and gas chromatographic analyses showed essentially complete conversion. To the charge was added 600 ml. of water, and the charge was steam stripped through a 5-plate Oldershaw column to a head temperature of 92° (pot temperature of 97°) to remove t-butanol as its aqueous azeotrope. The charge was cooled to 70°±10° and the layers separated; the lower (product) layer was returned to the reactor flask. To the amine was added 600 g. of 5% sodium chloride brine, and the charge was agitated at 95°±2° for 0.5 hour. The charge was separated after cooling to 90°; the product (324.8 g., 96.1% crude yield) was a clear yellow oil which solidified on cooling.

Analysis:
Calculated for mixture of

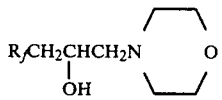

having an average molecular weight of 563:

Calc.: 1.78 meq amine/gram. Found: 1.81 meq amine/gram.

Preparation of N-type Betaines from N-(3-perfluoroalkyl 2-hydroxypropyl)morpholines After melting 50 parts (0.0905 mole) of N-(3-perfluoralkyl-2-hydroxypropyl)morpholines and adjusting the temperature to 30° C., 100 parts of glacial acetic acid were added. The charge temperature rose from 30° C. to 39° C. To the resultant solution was added 12.7 g. of 96.6% sodium chloroacetate (0.105 mole) and 0.4 g. potassium iodide (0.0024 mole). The charge was heated to 95°±2° C. and agitated at 95°±2° C. for 85.5 hours. The reaction mass was cooled to 25°±3° C. and filtered as quantitatively as possible; the sodium chloride filtered from the charge was acetone washed and air dried to give 3.9 parts (equivalent to a conversion of 73.6%). The material recovery, including salt, was 98.3%. Assuming solvent loss only, the product was a solution containing about 35% solids, the main constitutuent of which is a mixture of compounds having the formula:

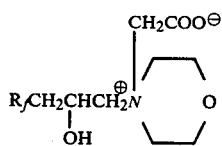

In water at 0.1, 0.01 and 0.001%, the betaines gave surface tensions (dynes/cm) of 17.4, 20.9 and 36,0, respectively.

EXAMPLE 2

The preparation of 3-perfluoroalkylpropylene iodohydrins and their precursors is described hereinabove.

Preparation of N,N-dimethyl(3-perfluoroalkyl-2-hydroxypropyl)amine

A mixture of 362.8 g. (0.6 mole) of 3-perfluoroalkylpropylene iodohydrins and 441 g. of t-butanol was warmed to 35°–40° to effect solution and then cooled to 23°, and 74 g. (0.66 mole) of 50% aqueous potassium hydroxide were added in eight equal increments at 0.5 hour intervals, the temperature being reduced to 5°±5° over the first 1.5 hours and held there. Approximately 20 minutes after the seventh KOH addition, 96.8 g. of 40% dimethylamine (0.86 mole) was added. After the charge had been agitated for 18 hours at 5°±5°, cooling was discontinued. The charge was allowed to come to 25°±3° and was agitated at that temperature for 20 hours. As at that point, gas chromatographic analysis showed that conversion of the iodohydrin to the amine was not quite complete, the charge was reheated to 53°±2° and agitated at that temperature for 6 hours. The charge was then cooled to 25°±3°, 8.3 g. sodium dihydrogen phosphate monohydrate (0.06 mole) were added to neutralize excess potassium hydroxide, and agitation at 25°±3° continued for 3 hours. To the charge was added 600 ml. of water, and the charge was steam stripped through a 5-plate Oldershaw column to a head temperature of 94° (pot temperature of 99° C.) to remove t-butanol as its aqueous azeotrope. The charge was cooled to 25°±5° C. and the layers separated; the lower (product) layer was returned to the reactor flask. To the amine was added 600 g. of 5% sodium chloride brine, and the charge was agitated at 90° to 95° for 0.5 hour. The charge was separated after cooling to 35° C.; the product (287.1 g., 92.4% crude yield) was an orange-yellow oil.

Analysis:

Calculated for mixture of

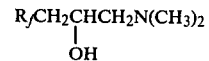

having an average molecular weight of 521.7:

Calculated: 1.92 meq amine/gram. Found: 1.93 meq amine/gram.

Preparation of N-type Betaines from N,N-dimethyl (3-perfluoroalkyl-2-hydroxypropyl)amines To 51 g. (0.0984 mole) of N,N-dimethyl(3-perfluoroalkyl-2-hydroxypropyl)amines was added 100 g. of glacial acetic acid, 13.8 g. of 96.6% sodium chloroacetate (0.114 mole) and 0.4 g. of potassium iodide (0.0024 mole). The charge was heated to 95°±2° and agitated at 95°±2° for a total of 67 hours. The reaction mass was cooled to 25°±3° and filtered as quantitatively as possible; the sodium chloride filtered from the charge was acetone washed and air dried, wt.=4.56 g. (equivalent to a conversion of 79.2%). The product was a solution containing about 38% solids, the principal constituent of which is mixture of compounds having the formula:

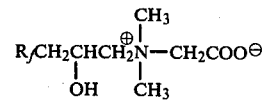

In water at 0.1, 0.01, and 0.001%, the betaines gave surface tensions of 16.6, 21.1 and 45.6 respectively.

I claim:

1. An amphoteric N-type betaine having surfactant properties represented by the formula:

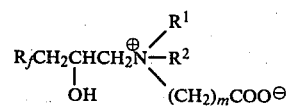

wherein $R_f$ is $C_4$–$C_{20}$ perfluoroalkyl;

$R^1$ and $R^2$ are methyl or, together with the N atom to which they are bonded, form a piperidino, morpholino, or N-alkyl ($C_1$–$C_4$) piperazino; and m is a whole number between 1 and 4; and mixtures thereof.

2. Mixtures of betaines of claim 1 wherein 80–90% of the $R_f$ groups contain 6 to 12 carbons.

3. Mixtures of claim 2 wherein 80–90% of said $R_f$ groups contain 6 to 10 carbons.

4. The betaine or mixtures of betaines of claim 1, 2 or 3 wherein the average of the chain lengths in the $R_f$ groups is 6 to 8 carbons.

* * * * *